(12) United States Patent  
Boland et al.

(10) Patent No.: US 8,637,503 B2
(45) Date of Patent: *Jan. 28, 2014

(54) PHENOTHIAZINE ENANTIOMERS AS AGENTS FOR THE PREVENTION OF BONE LOSS

(75) Inventors: Edward J. Boland, San Antonio, TX (US); Joe McDonough, Helotes, TX (US)

(73) Assignees: Board of Regents, The University of Texas System, Austin, TX (US); Southwest Research Institute, San Antonio, TX (US)

( * ) Notice: Subject to any disclaimer, the term of this patent is extended or adjusted under 35 U.S.C. 154(b) by 1402 days.

This patent is subject to a terminal disclaimer.

(21) Appl. No.: 10/556,878

(22) PCT Filed: May 17, 2004

(86) PCT No.: PCT/US2004/015416
§ 371 (c)(1),
(2), (4) Date: May 10, 2006

(87) PCT Pub. No.: WO2004/110458
PCT Pub. Date: Dec. 23, 2004

(65) Prior Publication Data
US 2006/0258650 A1  Nov. 16, 2006

Related U.S. Application Data

(60) Provisional application No. 60/471,155, filed on May 16, 2003.

(51) Int. Cl.
*A61K 31/5415* (2006.01)
*A61K 31/54* (2006.01)

(52) U.S. Cl.
USPC .................. 514/226.2; 424/400; 424/422

(58) Field of Classification Search
None
See application file for complete search history.

(56) References Cited

U.S. PATENT DOCUMENTS

| 2,519,886 | A | 2/1946 | Charpentier |
| 2,645,640 | A | 12/1951 | Charpentier |
| 3,100,772 | A | 8/1963 | Kantor et al. |
| 4,256,743 | A | 3/1981 | Goldhaber ................ 424/247 |

(Continued)

FOREIGN PATENT DOCUMENTS

| EP | 1 273 301 A2 | 1/2002 |
| EP | 1 181 933 A2 | 2/2002 |

(Continued)

OTHER PUBLICATIONS

Ponder et al, "Resolution of promethazine, ethopropazine, trimeprazine and trimipramine enantiomers on selected chiral stationary phases using high-performance liquid chromatography", Journal of Chromatography A, 692, pp. 173-182 (1995).*

(Continued)

*Primary Examiner* — Daniel Sullivan
*Assistant Examiner* — Barbara Frazier (57) ABSTRACT

Disclosed is the unexpected finding that enantiomers of phenothiazines, preferably the (+) enantiomer of promethazine, are particularly effective in inhibiting the bone resorbing cells, osteoclasts, thus providing new uses and methods for reducing bone loss and, e.g., treating periodontitis and osteoporosis. The invention provides a range of such uses, methods, medicaments and associated compositions and kits.

4 Claims, 9 Drawing Sheets

(56) References Cited

U.S. PATENT DOCUMENTS

| | | | |
|---|---|---|---|
| 4,703,052 A * | 10/1987 | Eggler et al. | 514/337 |
| 4,833,138 A | 5/1989 | Olney | |
| 4,883,666 A | 11/1989 | Sabel et al. | 424/422 |
| 5,114,719 A | 5/1992 | Sabel et al. | 424/422 |
| 5,601,835 A | 2/1997 | Sabel et al. | 424/424 |
| 5,883,128 A | 3/1999 | Yu et al. | 514/557 |
| 6,103,735 A | 8/2000 | Aslanian et al. | 514/290 |
| 6,451,341 B1 * | 9/2002 | Slaga et al. | 424/468 |
| 6,841,161 B1 * | 1/2005 | Passmore et al. | 424/400 |
| 2002/0151541 A1 | 10/2002 | Pairet et al. | 514/217.05 |
| 2002/0169146 A1 | 11/2002 | Gaddam et al. | 514/62 |
| 2002/0198231 A1 | 12/2002 | Nelson | 514/313 |

FOREIGN PATENT DOCUMENTS

| | | |
|---|---|---|
| GB | 806676 | 11/1956 |
| GB | 857547 | 12/1956 |
| WO | WO 97/02824 | 1/1997 |
| WO | WO 99/19313 | 4/1999 |
| WO | WO 00/50414 | 8/2000 |
| WO | WO 00/61111 | 10/2000 |
| WO | WO 02/062772 A1 | 8/2002 |
| WO | WO 03/105811 A2 | 12/2003 |
| WO | WO 2004/110458 A1 | 12/2004 |

OTHER PUBLICATIONS

Borsey et al, "Studies on Promethazine II. Antihistaminic Activity of its Optical Iosmers", Acta Physiologica, 15: 339-343 (1959).*

Rico et al. "Effects of Promethazine on Bone Mass and on Bone Remodeling in Ovariectomized Rats: A Morphometric, Densitometric, and Histomorphometric Experimental Study." Calcif Tissue Int, 1999; 65:272-275.

Jilka et al. "Increased bone formation by prevention of osteoblast apoptosis with parathyroid hormone." J Clin Invest, 1999; 104:439-446.

Dobigny et al. "H1 and H2 Histamine Receptors Modulate Osteoclastic Resorption by Different Pathways: Evidence Obtained by Using Receptor Antagonists in a Rat Synchronized Resorption Model." J Cell Physiol, 1997; 173:10-18.

Hall et al. "Phenothiazines are Potent Inhibitors of Osteoclastic Bone Resorption." Gen Pharmac, 1996; 27(5):845-848.

* cited by examiner

Control

Seeded — SEM: 200X

Unseeded — SEM: 200X

FIG. 5A

Promethazine $10^{-5}$ M

(+) enantiomer

(−) enantiomer

Racemate

FIG. 5B

Promethazine $10^{-6}$ M (+) enantiomer

(−) enantiomer

Racemate

FIG. 5C

Promethazine 10⁻⁷ M

(+) enantiomer (−) enantiomer

Racemate

PHENOTHIAZINE ENANTIOMERS AS AGENTS FOR THE PREVENTION OF BONE LOSS

The present application claims priority to U.S. provisional application Ser. No. 60/471,155, filed May 16, 2003, the entire disclosure of which application is specifically incorporated herein by reference without disclaimer. For the United States, Applicants reserve the right to claim priority to co-pending PCT application No. PCT/US03/02797, filed Jan. 31, 2003, and to U.S. provisional application Ser. No. 60/353,633, filed Jan. 31, 2002 and to U.S. provisional application Ser. No. 60/353,766, filed Jan. 31, 2002; the entire disclosures of which applications are specifically incorporated herein by reference without disclaimer irrespective of reserving the right to claim priority thereto.

BACKGROUND OF THE INVENTION

1. Field of the Invention

The present invention relates generally to the fields of osteoclasts and bone. The invention provides surprisingly effective methods for inhibiting osteoclasts, reducing bone loss and treating conditions such as periodontitis and osteoporosis by administering a phenothiazine enantiomer, preferably the (+) enantiomer of promethazine, and associated medicaments, compositions and kits.

2. Description of Related Art

The two major cell types that form and degrade bone are the osteoblast and the osteoclast, respectively. The improper functioning of such cells can produce aberrant bone metabolism, which is linked to the development of several human diseases and disorders, e.g., periodontitis and osteoporosis.

Osteoporosis is defined as compromised bone strength that leads to an increased risk of fracture. This condition results from the mis-regulation of the osteoblast and the osteoclast, thus disturbing the balance of bone formation and degradation.

Osteoporosis is a significant problem in the elderly, in individuals with genetic defects and in those who undergo prolonged space flight. In the weightless environment, bone loss occurs at approximately 2% per month, due to decreased osteoblast activity without alteration in osteoclast activity. Post-menopausal osteoporosis poses a considerable health problem. Significant bone loss in women occurs following estrogen removal, which is due to an increase in osteoclastic activity.

In the United States, osteoporosis is responsible for more than 1.5 million factures annually, including 300,000 hip fractures, 700,000 vertebral fractures, 250,000 wrist fractures and 300,000 fractures at other sites. The estimated national direct expenditure (hospitals and nursing homes) for osteoporotic and associated fractures was $17 billion in 2001, and the cost is rising.

Although there is no cure for osteoporosis, the following medications are approved by the FDA for postmenopausal women to prevent and/or treat osteoporosis: bisphosphonates, such as alendronate (brand name Fosamax®), risedronate (brand name Actonel®); calcitonin (brand name Miacalcin®); estrogen/hormone replacement therapy, including estrogens (brand names, such as Climara®, Estrace®, Estraderm®, Estratab®, Ogen®, Premarin® and others) and estrogens and progestins (brand names, such as Activella®, FemHrt®, Premphase®, Prempro® and others) and selective estrogen receptor modulators (SERMs), such as Raloxifene (brand name Evista®).

Unfortunately, all current treatment modalities suffer from certain drawbacks. For example, the available medications are all expensive and problematical to dose. Importantly, most of the current treatments have serious side effects that result in secondary problems. For example, estrogen treatment is associated with increased risk of cancers in females.

Accordingly, there remains in the art a need for improved methods for preventing or treating bone loss, particularly bone loss associated with osteoporosis. The development of methods to prevent or reduce bone loss with higher efficacy and lower risk of side effects is highly desirable, particularly if the methods could be developed at relatively low cost.

SUMMARY OF THE INVENTION

The present invention overcomes the foregoing deficiencies and solves certain long-felt needs in the art by providing improved uses and methods for preventing or treating bone loss, such as bone loss associated with periodontitis and osteoporosis. The invention particularly provides uses, medicaments and methods for reducing bone loss and, e.g., treating periodontitis and osteoporosis, by administering a biologically or therapeutically effective amount of only one enantiomer of a chiral phenothiazine, preferably the (+) enantiomer of promethazine or substituted promethazine derivatives. The (+) enantiomer of promethazine, for example, has been found to be surprisingly effective in comparison to the racemate and the (−) enantiomer.

Use of the phenothiazine and promethazine enantiomers according to the invention is believed to exert beneficial and anti-osteoporotic effects via osteoclast antagonism or inhibition. The invention thus provides methods of antagonizing or inhibiting osteoclasts by providing an effective inhibitory amount of a phenothiazine enantiomer, preferably the (+) enantiomer of promethazine (typically promethazine hydrochloride) or substituted promethazine derivatives. The invention further provides phenothiazine and promethazine enantiomers modified to increase their hydrophilic characteristic, thereby decreasing their blood-brain barrier penetration.

The effective inhibitory amounts and biologically and therapeutically effective amounts are amounts effective to inhibit osteoclasts and, preferably, amounts effective to reduce bone loss, thereby treating or preventing osteoporosis and other diseases related to bone loss, such as Paget's disease (osteitis deformans) and periodontal disease. Important advantages of the invention include high efficacy and decreased negative indications in comparison to the current methods for treating osteoporosis, as well as the low cost of treatment.

The uses, methods, medicaments, compositions, kits and combinations encompassed by the invention, and various exemplary and certain preferred embodiments thereof, are described in the present specification and the appended claims.

In particular embodiments, the invention provides methods of inhibiting osteoclasts, comprising contacting a population of cells comprising osteoclasts with a biologically effective amount of a composition comprising a substantially purified enantiomer of a chiral phenothiazine, preferably the (+) enantiomer of promethazine or a substituted promethazine derivative.

Although the invention has significant in vivo uses, particularly as the racemic mixtures are currently used in the clinic, the invention also has in vitro uses in the inhibition of osteoclasts in cell populations and tissue samples ex vivo. For example, in maintaining the integrity of bone tissue samples prior to use in bone grafts and such like.

Accordingly, the invention provides methods of inhibiting osteoclasts, comprising contacting a population of cells comprising osteoclasts in vitro with a biologically effective amount of a composition comprising a substantially purified enantiomer of a chiral phenothiazine, preferably the (+) enantiomer of promethazine or a substituted promethazine derivative. The population of cells comprising osteoclasts may be a population of cultured cells or an in vitro bone tissue sample.

Where the population of cells comprising osteoclasts is a substantially intact bone tissue sample, such a substantially intact bone tissue sample may thus be an in vitro bone tissue sample or a bone tissue sample within an animal or patient in vivo. In embodiments where the population of cells comprising osteoclasts is located within an animal, the composition comprising a biologically effective amount of a substantially purified enantiomer of a chiral phenothiazine, preferably the (+) enantiomer of promethazine or a substituted promethazine derivative, is administered to the animal or patient, thereby contacting the cell population or tissue sample in situ.

The invention further includes methods of, and uses in, inhibiting osteoclastic resorption of bone, bone tissue and bone tissue samples. The methods generally comprise contacting a bone tissue sample with a composition comprising a substantially purified enantiomer of a chiral phenothiazine, preferably the (+) enantiomer of promethazine or a substituted promethazine derivative, in an amount effective to inhibit osteoclasts in the bone tissue sample, thereby inhibiting osteoclastic resorption of bone tissue.

Again, the bone tissue sample may be an in vitro bone tissue sample or a bone tissue sample within an animal or patient in vivo. Where the bone tissue sample is maintained ex vivo or in vitro, the methods comprise contacting an in vitro bone tissue sample with the chiral phenothiazine composition in an amount effective to inhibit osteoclasts in the bone tissue sample, thereby inhibiting osteoclastic resorption of bone tissue in vitro.

Where the bone tissue sample is located within an animal, the methods comprise providing to an animal or patient exhibiting or at risk for osteoclastic resorption of bone, a composition comprising a substantially purified enantiomer of a chiral phenothiazine, preferably the (+) enantiomer of promethazine or a substituted promethazine derivative, in an amount effective to inhibit osteoclasts in the animal or patient, thereby inhibiting osteoclastic resorption of bone in the animal or patient.

Important aspects of the invention are methods of, and uses in, treating or preventing bone loss. Methods of treating or preventing bone loss generally comprise providing to an animal or patient exhibiting or at risk for bone loss a biologically or therapeutically effective amount of a composition comprising a substantially purified enantiomer of a chiral phenothiazine, preferably the (+) enantiomer of promethazine or a substituted promethazine derivative.

Similar embodiments of the invention concern use of a composition comprising a substantially purified enantiomer of a chiral phenothiazine, preferably the (+) enantiomer of promethazine or a substituted promethazine derivative, in the manufacture of a medicament for use in inhibiting osteoclasts for treating or preventing a disease or condition associated with bone loss.

Other methods of the invention are methods of reducing bone loss, comprising providing to an animal or patient exhibiting bone loss an amount of a composition comprising a substantially purified enantiomer of a chiral phenothiazine, preferably the (+) enantiomer of promethazine or a substituted promethazine derivative, effective to treat bone loss in the animal or patient.

Related uses of the invention concern the manufacture of a medicament for use in inhibiting osteoclastic resorption of bone, the manufacture of a medicament for treating or preventing bone loss, and the manufacture of a medicament for treating bone loss. A particular use of the invention is the use of a composition comprising a substantially purified enantiomer of a chiral phenothiazine, preferably the (+) enantiomer of promethazine or a substituted promethazine derivative, in the manufacture of a medicament for use in treating or preventing a disease or condition associated with bone loss.

In the methods and uses of the invention, the animal or patient may have or be at risk for developing periodontitis, including chronic destructive periodontal disease. Accordingly, the invention provides methods of treating or preventing periodontitis, comprising providing to an animal or patient having or at risk for developing periodontitis a therapeutically effective amount of a composition comprising a substantially purified enantiomer of a chiral phenothiazine, preferably the (+) enantiomer of promethazine or a substituted promethazine derivative. In the treatment methods, the methods comprise providing to an animal or patient with periodontitis a therapeutically effective amount of a composition comprising the chiral phenothiazine, preferably a substantially purified (+) enantiomer of promethazine. In such methods, the biologically and therapeutically effective amounts are typically amounts effective to treat periodontitis upon administration of the composition to the animal or patient.

Related uses of the invention concern the manufacture of a medicament for use in treating or preventing periodontitis or chronic destructive periodontal disease and the manufacture of a medicament for treating periodontitis or chronic destructive periodontal disease.

The animal or patient to be treated by the methods and uses of the invention may have or be at risk for developing osteoporosis. The invention thus provides methods of treating or preventing osteoporosis, comprising providing to an animal or patient having or at risk for developing osteoporosis a therapeutically effective amount of a composition comprising a substantially purified enantiomer of a chiral phenothiazine, preferably the (+) enantiomer of promethazine or a substituted promethazine derivative. In the treatment methods, the methods comprise providing to an animal or patient with osteoporosis a therapeutically effective amount of a composition comprising the chiral phenothiazine, preferably a substantially purified (+) enantiomer of promethazine.

In such methods, the biologically and therapeutically effective amounts are typically amounts effective to treat osteoporosis upon administration of the composition to the animal or patient. Such "an effective amount" is therefore termed "an anti-osteoporotic amount".

Although the treatment of osteoporosis in all settings is encompassed by the invention, the treatment of osteoporosis is particularly important in post-menopausal females, which therefore form a preferred treatment group within the methods and uses of the invention.

Related uses of the invention concern the manufacture of a medicament for use in treating or preventing osteoporosis, the manufacture of a medicament for treating osteoporosis and the manufacture of a medicament for treating osteoporosis in post-menopausal females.

The invention further provides kits and therapeutic kits, which generally comprise, in at least a first container:
(a) a biologically or therapeutically effective amount of a substantially purified enantiomer of a chiral phenothiazine, preferably the (+) enantiomer of promethazine or a substituted promethazine derivative; and (b) a biologically or therapeutically effective amount of a second, distinct anti-osteoclastic or anti-osteoporotic agent.

The biologically or therapeutically effective amounts of the chiral phenothiazines of the kits are typically amounts effective to inhibit osteoclasts, inhibit bone resorption, treat or prevent periodontitis, and/or treat or prevent osteoporosis and such like. In the kits, the chiral phenothiazine and the second, distinct anti-osteoclastic or anti-osteoporotic agent may be comprised within a single container, such as an admixture, or may be comprised separately, within distinct containers.

The kits of the invention may further comprise instructions for using the kits to inhibit osteoclasts, inhibit bone resorption, treat or prevent periodontitis, treat or prevent osteoporosis and/or manufacture a medicament for use in any such preventative or treatment modalities. The instructions may be written, or in electronic or computerized form.

In each of the uses, methods, medicaments, compositions, kits and combinations of the invention, the use of an enantiomerically pure enantiomer of a chiral phenothiazine is preferred. A range of chiral phenothiazines may be used in the invention, such as wherein the chiral phenothiazine has the structure:

wherein $R^1$, $R^2$, and $R^3$ have a size substantially equivalent to an alkyl radical having 6 or fewer carbon atoms;

X is selected from the group consisting of a linear or branched alkyl radical and a linear or branched alkenyl group having from about 1 to about 5 carbon atoms; and $R^4$ is a tertiary amine or thiol radical having a structure selected from the group consisting of N—$(R^5)_2$ and S—$R^5$ wherein $R^5$ comprises the same or different entities independently selected from the group consisting of hydrogen, alkyl radicals and alkenyl radical having from about 1 to about 4 carbon atoms, cyclic alkylene groups and heterocyclic alkylene groups comprising a heterocyclic element selected from the group consisting of nitrogen and sulfur.

In certain preferred embodiments, referring to the foregoing structure and definitions, $R^1$, $R^2$, and $R^3$ independently are an ionizable group selected from the group consisting of ammonium, sulfonium, and phosphonium groups and esters thereof. The esters preferably comprise linear or branched alkyl groups comprising from about 1 to about 5 carbon atoms.

In other preferred embodiments, referring to the foregoing structure and definitions, $R^1$, $R^2$, and $R^3$ independently are selected from hydrogen, a hydroxyl radical, an alkoxy radical comprising a branched or unbranched alkyl radical having a total of from about 1 to about 6 carbon atoms, an acyloxy radical comprising a branched or unbranched alkyl radical having a total of from about 1 to about 6 carbon atoms, a substituted or unsubstituted branched or unbranched alkyl radical having a total of from about 1 to about 6 carbon atoms, a substituted or an unsubstituted phenyl radical or a substituted or an unsubstituted benzyl radical wherein the substituted radicals comprise substituents selected from the group consisting of hydroxyl radicals, halogens, alkyl radicals having a total of from about 1 to about 6 carbon atoms, cyclic alkylene groups and heterocyclic alkylene groups comprising a heterocyclic element selected from the group consisting of nitrogen and sulfur.

In particular embodiments, $R^5$ is selected from the group consisting of alkyl radicals and alkenyl radical having from about 1 to about 3 carbon atoms.

Particular chiral phenothiazines for use in the invention are promethazine, ethopropazine, propiomazine and trimeprazine. Where the chiral phenothiazine is an ethopropazine, the invention concerns the use of a substantially purified (−) enantiomer of ethopropazine.

In particularly preferred embodiments, the chiral phenothiazine of the uses, methods, medicaments, compositions, kits and combinations of the invention is a substantially purified (+) enantiomer of promethazine.

BRIEF DESCRIPTION OF THE DRAWINGS

The following drawings form part of the present specification and are included to further demonstrate certain aspects of the present invention. The invention may be better understood by reference to the drawings in combination with the detailed description of specific embodiments presented herein.

DESCRIPTION OF ILLUSTRATIVE EMBODIMENTS

In adults, bone tissue undergoes a continual process of renewal, which is orchestrated by osteoblasts and osteoclasts, specialized cell types that originate from progenitors residing in the bone marrow. The numbers and activity of osteoblasts and osteoclasts is important for bone homeostasis, as changes in their number and activity result in imbalances between bone formation and bone resorption, which can lead to systemic and/or localized bone diseases, including periodontitis and osteoporosis.

Bone mass can be increased by intermittent parathyroid hormone (PTH) administration. It has been reported that daily PTH injections in mice with either normal bone mass or osteopenia due to defective osteoblastogenesis increased bone formation without affecting the generation of new osteoblasts (Jilka et al., 1999). These authors reported that PTH increased the life-span of mature osteoblasts by preventing their apoptosis; and the anti-apoptotic effect was said to be sufficient to account for the increase in bone mass, as confirmed in vitro using rodent and human osteoblasts and osteocytes (Jilka et al., 1999). Jilka et al. (1999) thus suggested the use of anti-apoptotic strategies to treat osteoporosis and other pathological conditions in which bone mass diminution compromises functional integrity.

Periodontitis can result when inflammation or infection of the gums (gingivitis) is untreated and/or treatment is delayed. Infection and inflammation typically spreads from the gums (gingiva) to the ligaments and bone that support the teeth. Loss of support causes the teeth to become loose and eventually fall out. Periodontitis is the primary cause of tooth loss in adults.

During periodontitis, plaque and tartar accumulate at the base of the teeth. Inflammation causes a pocket to develop between the gums and the teeth, which fills with plaque and tartar. Soft tissue swelling traps the plaque in the pocket. Continued inflammation causes destruction of the tissues and bone surrounding the tooth. Bacteria in plaque cause infection, which can develop into a tooth abscess, further increasing the rate of bone destruction.

In addition to the use of PTH to augment bone mass in osteoporosis and associated conditions, it has recently been reported that PTH protects against periodontitis-associated bone loss (Barros et al., 2003). In these studies, Barros et al., (2003) demonstrated that intermittent administration of PTH blocked the alveolar bone loss observed in rats in a ligature model of periodontitis. These studies therefore show that restoring the balance between osteoblasts and osteoclasts, in this case by inhibiting apoptosis of osteoblasts, is effective in treating periodontitis.

The bisphosphonate compound, incadronate (YM175, disodium cycloheptylamino-methylenediphosphonate monohydrate), has been suggested to prevent the bone resorption associated with periodontitis by inhibiting osteoclast activity. Tani-Ishii et al., (2003) recently reported that incadronate was effective in preventing periodontal destruction in rats with *Porphyromonas gingivalis*-induced periodontitis. In controlled studies, it was shown that incadronate increased the bone mineral density and prevented periodontal ligament destruction in rats with *P. gingivalis* infections (Tani-Ishii et al., 2003). These studies therefore complement those described above, showing that compounds that inhibit osteoclast activity are able to treat periodontitis. Unfortunately, as with osteoporosis, the agents currently available for use in such treatment all suffer from certain drawbacks, including serious side effects.

Whilst periodontitis takes a toll in healthcare in the developed world, osteoporosis is a very significant problem. In the United States, the estimated national direct expenditures for osteoporotic and associated fractures was $17 billion in 2001. One of the agents approved for use in treating osteoporosis is promethazine (PMZ). In administering promethazine to human subjects, Tyan (1993) observed a 3% annual gain in spinal bone mass in post-menopausal women with a dosage of 50 mg/day promethazine associated with estrogens. Rico et al. (1999) also reported on the effects of promethazine on bone loss in rats (Table 1, taken from Table 1 in Rico et al., 1999).

TABLE 1

The Effects of Promethazine on Bone Loss in Rats

| | Controls | OVX | OVX + PROM | Sham-OVX |
|---|---|---|---|---|
| N | 15 | 15 | 15 | 15 |
| Initial weight g | 242 ± 28 | 252 ± 26 | 253 ± 17 | 257 ± 12 |
| Final weight g | 305 ± 22 | 327 ± 31[a] | 318 ± 26 | 293 ± 18 |
| Femur mm | 33.6 ± 0.4 | 33.8 ± 1.1 | 34.5 ± 0.7 | 34.0 ± 0.7 |
| Femur mg | 720 ± 52 | 679 ± 68 | 716 ± 38 | 704 ± 41 |
| F-BMC mg | 390 ± 31 | 292 ± 36[b] | 336 ± 30 | 346 ± 21 |
| Z score F-BMC | 0.1 ± 0.9 | −3.1 ± 1.1[b] | −1.7 ± 0.9 | −1.4 ± 0.6 |
| F-BMD mg/cm$^2$ | 135 ± 11 | 113 ± 13[c] | 125 ± 14 | 125 ± 9 |
| F-BMC/BW mg/g | 1.28 ± 0.03 | 0.90 ± 0.09 | 1.06 ± 0.06 | 1.18 ± 0.07 |
| Vertebra mm | 6.2 ± 0.2 | 6.2 ± 0.6 | 6.3 ± 0.3 | 6.1 ± 0.2 |
| Vertebra mg | 249 ± 14 | 217 ± 31[d] | 253 ± 24 | 241 ± 23 |
| V-BMC mg | 116 ± 13 | 86 ± 18[d] | 100 ± 10 | 111 ± 12 |
| V-BMD mg/cm$^2$ | 111 ± 8 | 101 ± 8[d] | 108 ± 6 | 112 ± 7 |
| Cn-BV-TV % | 19.9 ± 6.6 | 8.6 ± 4.1[c] | 12.5 ± 5.6 | 24.2 ± 5.9 |
| Tb-N mm$^{-1}$ | 2.9 ± 0.6 | 1.6 ± 0.6[c] | 2.1 ± 0.7 | 3.0 ± 0.2 |
| Tb-Th μm | 68.2 ± 19.6 | 52.3 ± 9.0 | 57.5 ± 7.3 | 70.1 ± 16.6 |
| Tb-Sp μm | 285 ± 70 | 857 ± 281[c] | 477 ± 215 | 253 ± 38 |

Femur bone mineral content and density (F-BMC mg and F-BMD mg/cm$^2$); 5$^{th}$ lumbar vertebral bone mineral content and density (V-BMC mg and V-BMD mg/cm$^2$); femur cancellous bone volume (Cn-BV/TV %); trabecular number (Tb-N mm$^{-1}$); trabecular thickness (Tb-Th μm); and trabecular separation (Tb-Sp μm); ovariectomized rats (OVX); promethazine-treated ovariectomized rats (OVX + PROM); and untreated Sham-ovariectomized rats (Sham-OVX).
[a]P = 0.001 vs. Sham-OVX;
[b]P < 0.0001 vs. others;
[c]P < 0.0005 vs. others;
[d]P < 0.0005 vs. OVX + PROM.
According to ANOVA with post hoc Bonferroni-Dunn test.

Taken from Table 1 in Rico et al., 1999, specifically incorporated herein by reference.

Promethazine is also used as an anti-emetic, anti-histamine and anti-psychotic agent The predominant mode of action is antagonism of histamine receptors. There are different histamine receptors, including histamine receptor 1 ($H_1$) and histamine receptor 2 ($H_2$). Promethazine is a member of the phenothiazines. Primarily anti-histamines, these compounds are promiscuous drugs and have been shown to be antagonists of the muscarinic cholinergic and dopamine receptors, albeit with lower affinity. Sedation is significant at concentrations achieved from therapeutic dosages. The sedative effects of promethazine require direct CNS interaction. FDA approval for promethazine was issued in 1954.

U.S. Pat. No. 4,256,743, specifically incorporated herein by reference, concerns methods for inhibiting bone resorption by orally administering $H_1$-blocking phenothiazines, including promethazine hydrochloride. In particular, the patent describes methods for inhibiting bone resorption in mammals suffering from osteoporosis or chronic destructive periodontal disease by administering specified amounts of an $H_1$-blocking anti-histamine compound ($H_1$ antagonist) in the form of an $H_1$-blocking phenothiazine, $H_1$-blocking ethylenediamine or $H_1$-blocking indene. The amounts specified for $H_1$-blocking phenothiazines are 25-50 mg/day.

In developing the present invention, the inventors reasoned that it was important to consider the implications resulting from the fact that promethazine is chiral. "Chiral" or optically active compounds exist in two forms: the (+) form and the (−) form. The (+) and (−) descriptors relate to how the enantiomers rotate the plane of plane-polarized light. The particular forms of chiral compounds are termed stereoisomers or enantiomers. A combination of the two forms is termed the racemate or racemic mixture.

Prior to the present invention, the clinical uses of promethazine, including the use of promethazine as an osteoporosis inhibitor, as in U.S. Pat. No. 4,256,743, utilized the compound as a racemic mixture. Indeed, the (+) form and the (−) form have been shown to be present at a ratio of 50:50 in clinical samples. The histamine receptor is chiral sensitive. Enantiomers of promethazine have been described in the literature in reference to combination pharmaceuticals (U.S. Pat. No. 6,103,735; U.S. patent application 2002/0151541; and U.S. patent application 2002/0198231). Such combined pharmaceuticals have been proposed for use in treating asthma and allergic conditions, respiratory tract diseases and Parkinson's disease. However, prior to the present invention, there was no information concerning the chiral sensitivity of promethazine's effects on osteoclasts.

Figure 1:
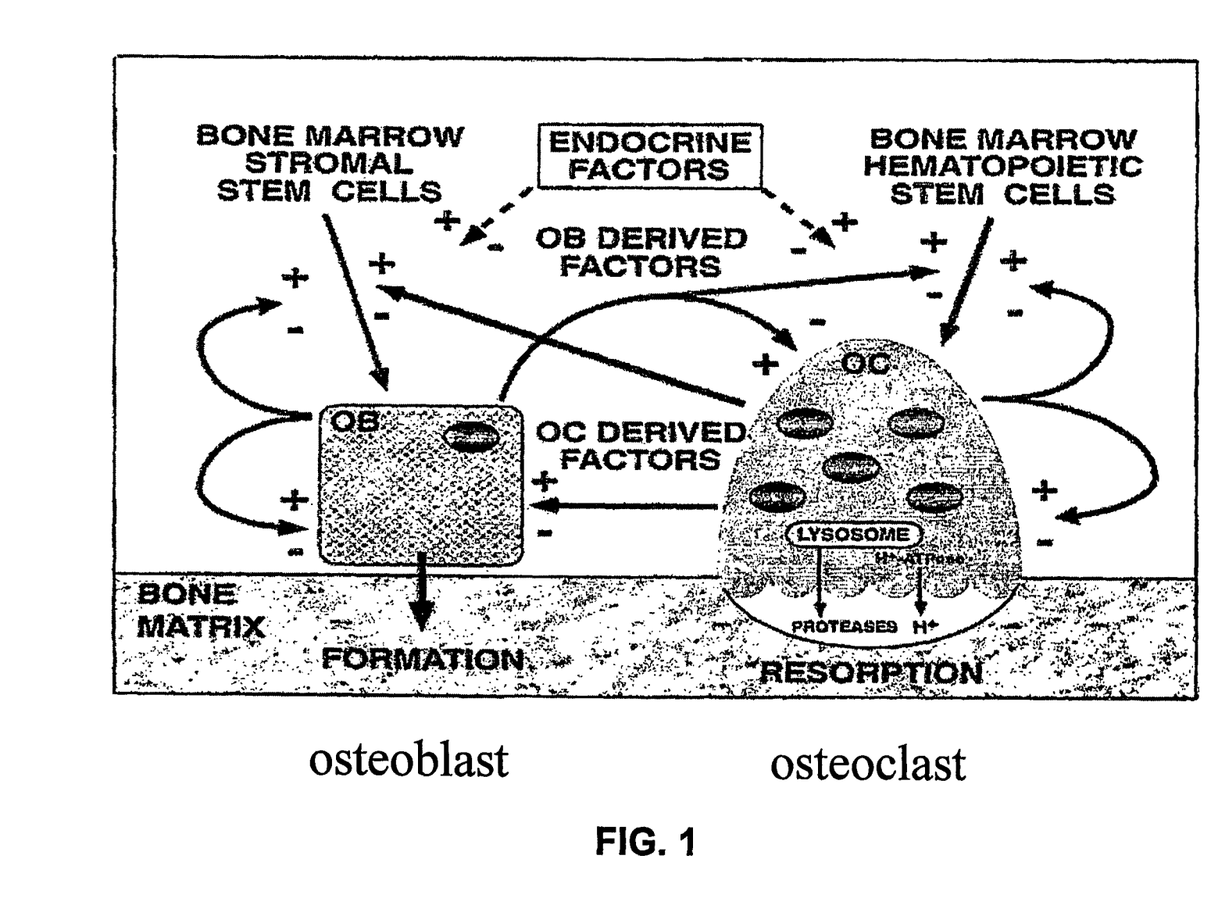
FIG. 1. Bone is a complex, highly regulated tissue composed of cells and calcified matrix.
Figure 2:
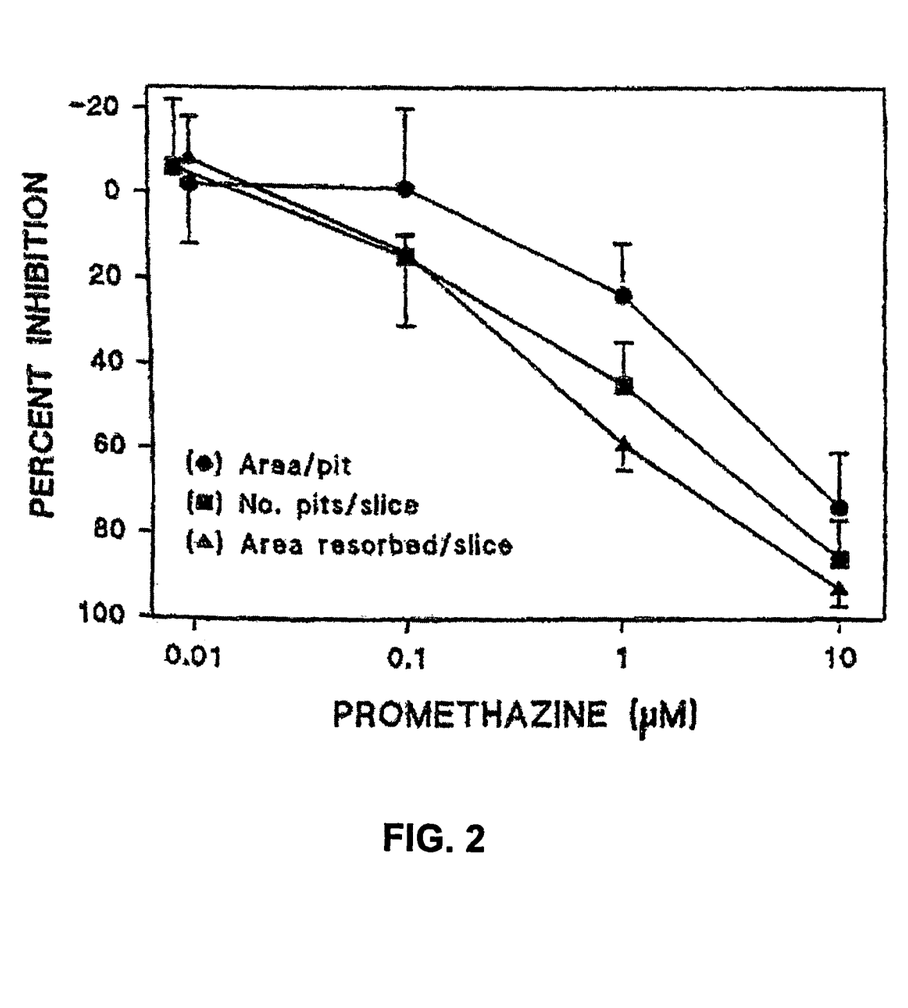
FIG. 2. A racemic mixture of promethazine inhibit bone resorption in vitro (taken from Hall and Schaueblin, 1994).
Figure 3:
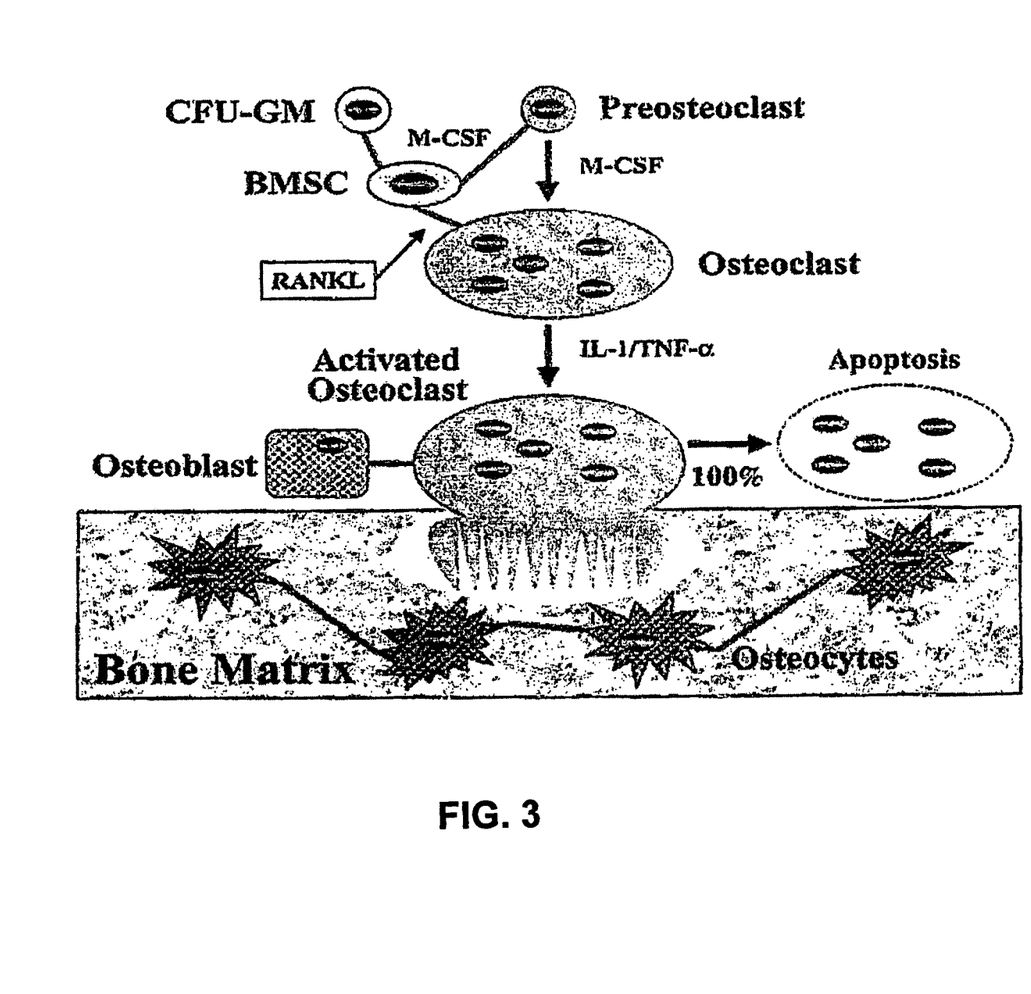
FIG. 3. Osteoclast physiology and biology.
Figure 4:
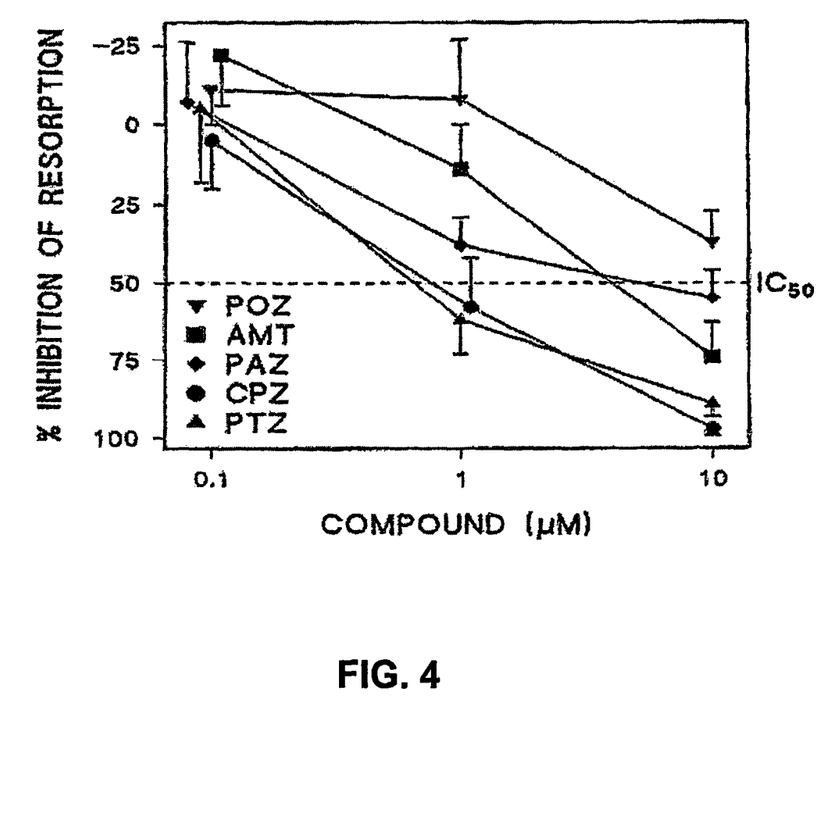
FIG. 4. Effect of phenothiazine analogues on osteoclastic bone resorption. The compounds were added at the start of the 24-h bone slice assay. The results shown are the mean±SEM of three separate studies for each compound tested (15 bone slices per point). The control area resorbed per bone slice value (mean±SEM) for a total of 15 studies was 7570±910 m² (taken from Schaeublin et al., 1996).
Figure 5A:
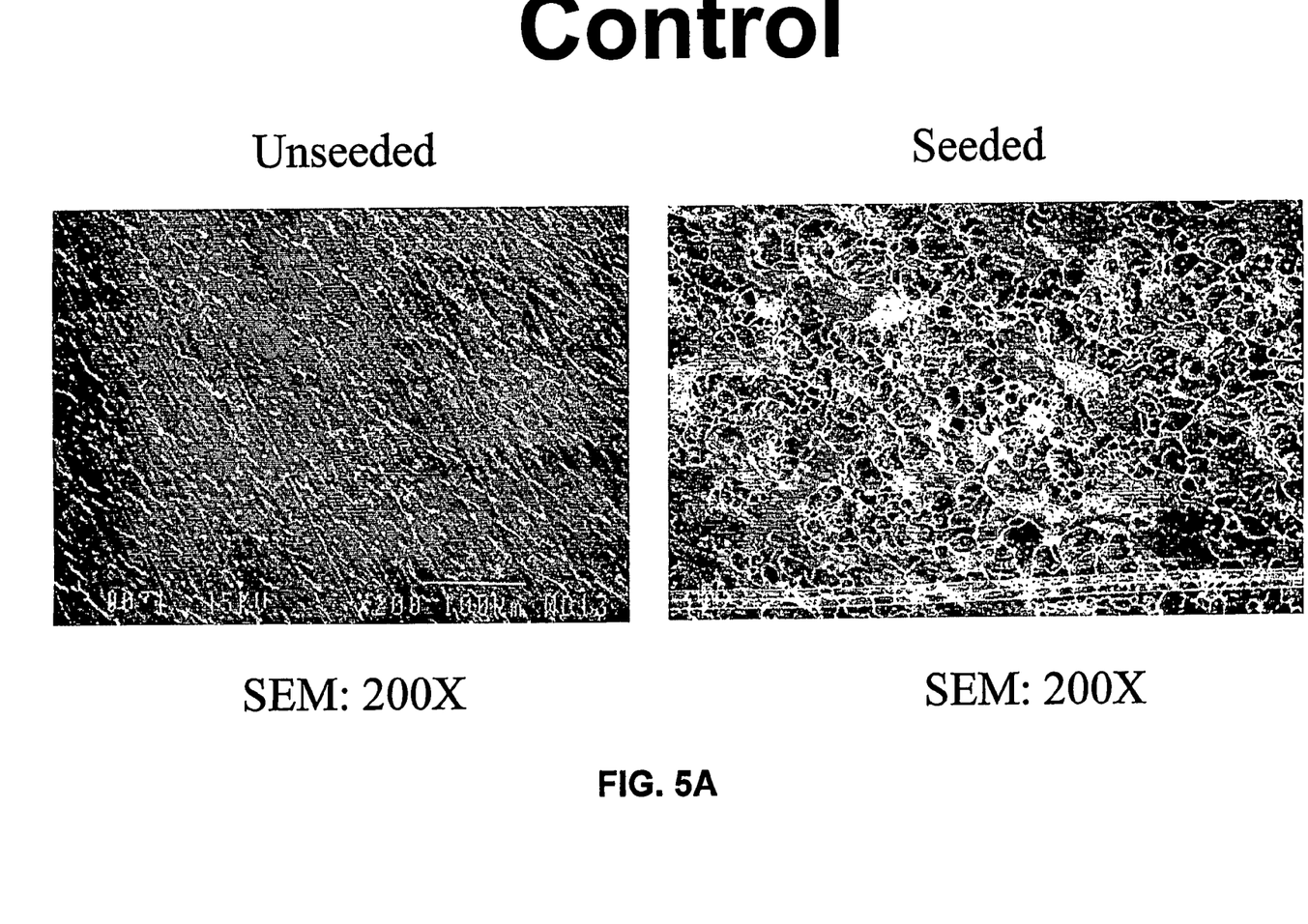
FIG. 5A, FIG. 5B, FIG. 5C and FIG. 5D. Effects of the racemic mixture and the (+) and (−) enantiomers of promethazine on osteoclast resorption at $10^{-5}$ M, $10^{-6}$ M and $10^{-7}$ M in controlled studies using an osteoclast resorption assay.
Figure 5B:
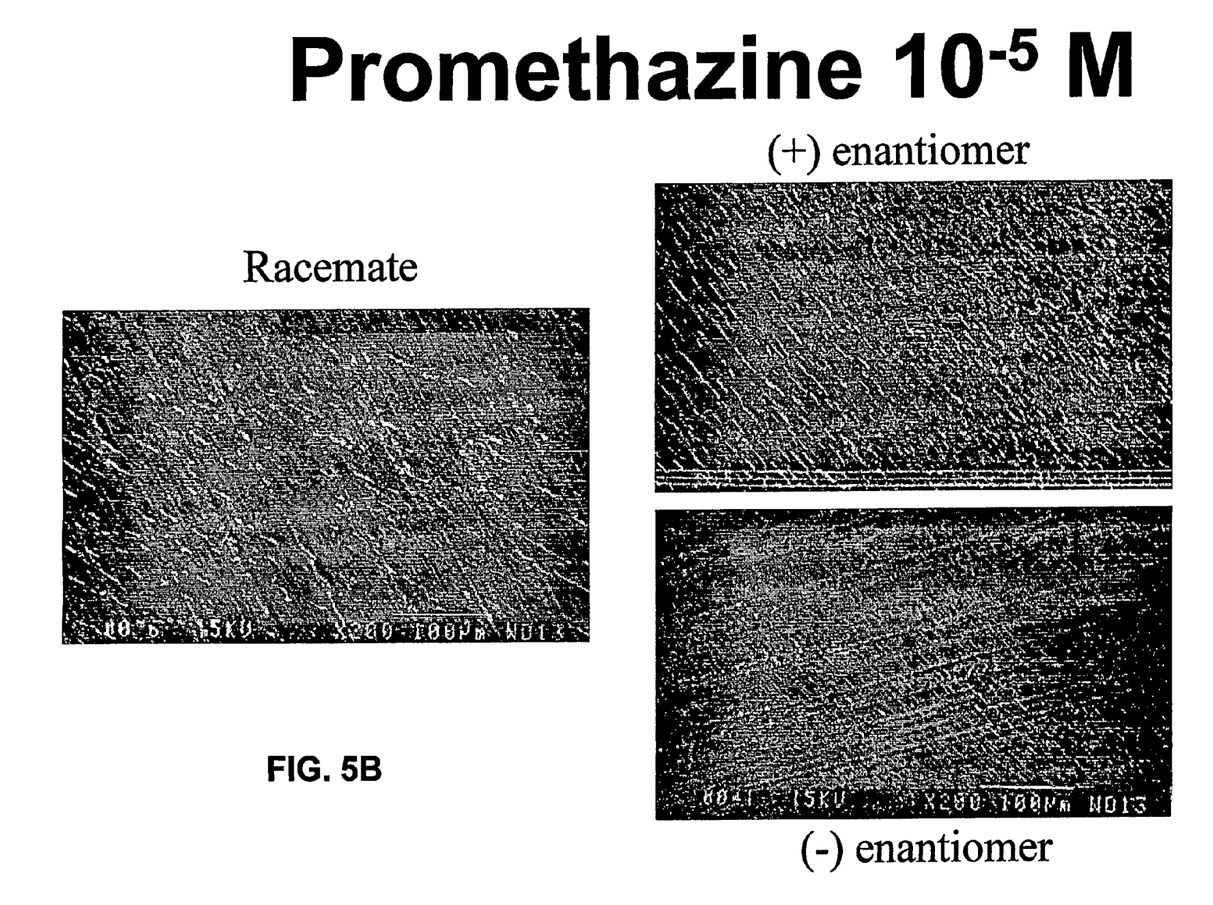
Figure 5C:
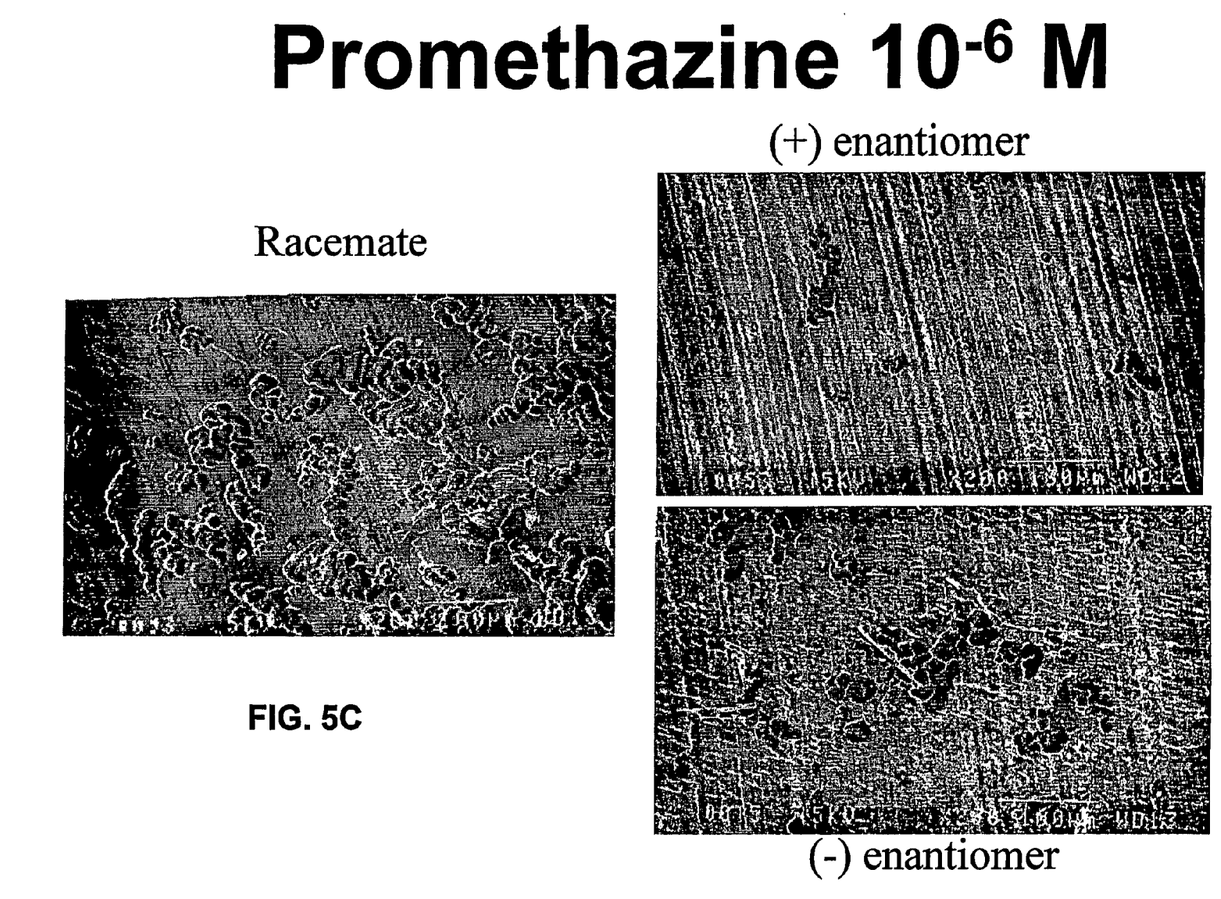
Figure 5D:
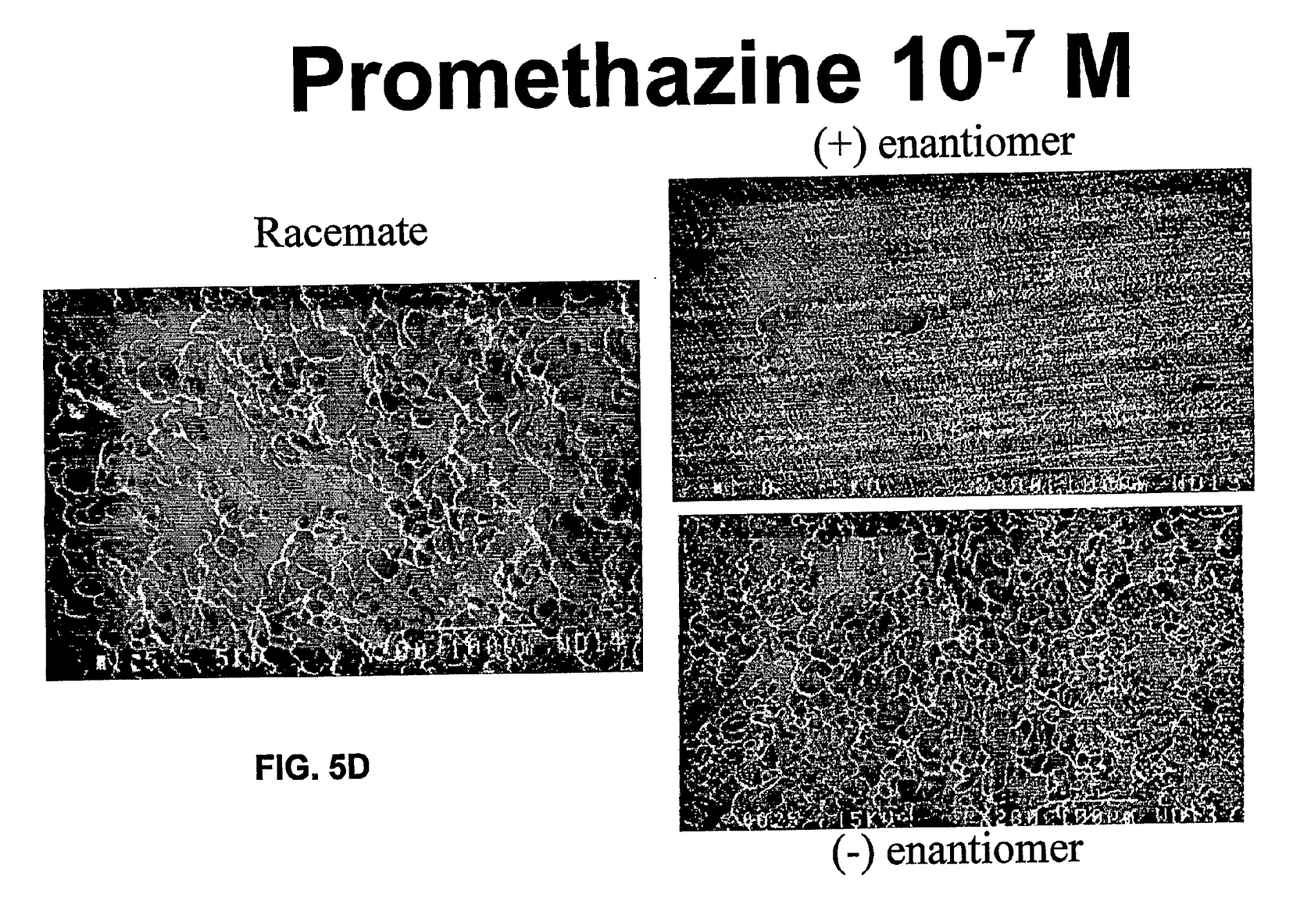

The inventors therefore re-evaluated what was known about promethazine prior to this invention. In vitro, increasing concentrations of promethazine had been shown to inhibit bone resorption (FIG. 2, from Hall and Schaueblin, 1994). Osteoporosis results from the dysregulation of osteoblasts, cells that form bone, and osteoclasts, cells that degrade bone (FIG. 3). Dobigny and Safar (1997) reported on the anti-histamine actions of certain $H_1$ receptor antagonists and $H_2$ receptor antagonists (Table 2, taken from Table 1 in Dobigny and Safar, 1997). As to the non-anti-histamine actions, Schaeublin et al. (1996) reported the effect of phenothiazine analogues on osteoclastic bone resorption in a 24-h bone slice assay (FIG. 4, from Schaeublin et al., 1996).

TABLE 2

Anti-Histamine Actions of $H_1$ and $H_2$ Receptor Antagonists

|  | RS | Total Osteoclasts | Active Osteoclasts | Inactive Osteoclasts | OBIT |
|---|---|---|---|---|---|
| Sham (n = 8) | 32.4 ± 2.7 | 19.1 ± 1.9 | 14.1 ± 1.3 | 5.0 ± 0.7 | 23.3 ± 1.1 |
| Mepyramine (n = 8) | 17.6 ± 1.3*** | 15.3 ± 1.5 | 9.6 ± 0.7* | 5.7 ± 0.8 | 18.4 ± 0.8** |
| Cimetidine (n = 8) | 14.4 ± 2.0** | 9.4 ± 1.4**, **** | 6.2 ± 0.8***, ***** | 3.1 ± 0.7 | 24.7 ± .9*, **** |
| Kruskal-Wallis test | H = 15.39 | H = 11.19 | H = 16.57 | H = 4.41 | H = 7.70 |
|  | P = 0.005 | P = 0.0032 | P = 0.0003 | NS | P = 0.0212 |

The table shows modifications of resorption parameters induced by mepyramine ($H_1$ receptor antagonist) and cimetidine ($H_2$ receptor antagonist) at the peak of resorption. The peak of bone resorption is 4 days in the synchronized model of resorption used; active osteoclasts are on-bone cells, and inactive osteoclasts are off-bone cells. OBI is the mean interface of the active cells with the bone surface.
Group comparisons were performed by using the Mann-Whitney U Test.
*Different from controls, P < 0.05.
**Different from controls, P < 0.01.
***Different from controls, P < 0.001.
****Different from the mepyramine group, P < 0.05.
*****Different from the mepyramine group, P < 0.01.

Taken from Table 1 in Dobigny and Safar, 1997, specifically incorporated herein by reference.

From their observations, the inventors therefore realized that for the $H_1$ antagonists, the non-histamine pathway appears to be the primary pathway. Thus, promethazine primarily inhibits osteoclastic resorption of bone via a histamine independent pathway; although a histamine dependent pathway may also be involved. As the mechanism of action of promethazine in the present invention is primarily independent of histamine inhibition, it is thus different to that underlying U.S. Pat. No. 4,256,743.

The chiral nature of the promethazine molecule suggested to the present inventors that only one of the enantiomers may be responsible for the biological activity observed for the racemic mixture. This proved to be the case, and the present application shows that activity resides in the (+) enantiomer and, surprisingly, that the (+) enantiomer has a three fold higher efficacy for osteoclast inhibition than the racemate and the (−) enantiomer in controlled studies. As used herein, the terms (+) and (−) enantiomer refer to optical rotation as measured in water.

In testing the (+) enantiomer for cytotoxicity, the inventors determined that it did not have any significant increase in cytotoxicity compared to the racemic mixture (the same was also true for the (−) enantiomer). The increased activity, without any increase in cytotoxicity, therefore makes the (+) enantiomer of promethazine ideal for treatment in place of the racemic mixture. The present invention therefore provides improved methods of inhibiting osteoclasts, reducing bone loss and treating or preventing periodontitis, osteoporosis and associated disorders by administering the (+) enantiomer of promethazine and, in light of the studies herein and the present disclosure, purified enantiomers of other chiral phenothiazines.

Although (+) and (−) are descriptors of how the enantiomers rotate plane polarized light, the terms R and S describe the absolute configuration. Enantiomers are also described using the terms D and L. The R isomer is the + in the case of promethazine. In other chiral phenothiazines in which the structures more closely resemble promethazine, weak R enantiomers are likely to be active, since this part of the molecule seems to influencing binding. As a histamine dependent pathway may also be involved in the inhibition of osteoclastic resorption of bone by phenothiazines, and the inventors determined that the major anti-histamine activity associated with ethopropazine resides in the (−) enantiomer, the (−) enantiomer of ethopropazine is also contemplated for use in the present invention. In any event, in light of the studies herein, particularly the successful working embodiments and the discriminatory assays described in detail, the enantiomer of any phenothiazine with activity in the inhibition of osteoclasts may now be determined and such an enantiomer used in the methods, medicaments, uses, compositions, combinations and kits of the present invention.

Within the substantially purified enantiomer compositions for use in the present invention, those consisting essentially of the active enantiomer will be particularly preferred, up to and including compositions comprising essentially or substantially the enantiomerically pure active enantiomer. In all embodiments, the (+) enantiomer of promethazine is still currently most preferred.

It will be understood that the terms "composition comprising a substantially purified enantiomer", "composition consisting essentially of an active enantiomer", "composition comprising essentially or substantially an enantiomerically pure active enantiomer", "composition comprising an enantiomerically pure active enantiomer of a phenothiazine", "composition comprising an enantiomerically pure (+) enantiomer of promethazine", and like terms, as used herein, refer to the composition and purity of the active enantiomer as opposed to the other enantiomer, such as the purity of the (+) enantiomer of promethazine as opposed to the (−) enantiomer of promethazine. Such terms do not exclude the presence of other components in the composition "comprising" the active enantiomer, such as the (+) enantiomer of promethazine, such as pharmaceutical diluents or components or other biological or therapeutic agents, particularly second agents for treating bone loss or osteoporosis.

Substantially enantiomerically pure and enantiomerically pure compounds can be prepared by those of ordinary skill in the art without undue experimentation in light of the present disclosure. U.S. Pat. No. RE 38334 (re-issue of U.S. Pat. No. 6,020,506) is specifically incorporated herein by reference for the purpose of describing and enabling the preparation of compositions comprising enantiomerically pure compounds per se.

Although phenothiazines and promethazine are approved for human administration, and available commercially, the present inventors generally do not recommend commercially available forms as starting materials. However, if the source of an active agent for use in the invention is a commercial tablet, then the mixture obtained from the tablet should preferably be treated to provide the active ingredient relatively free, preferably substantially free of the non-active components.

Methods of purification will be well known to those of ordinary skill in light of the present disclosure, and may include, e.g., dissolution of the mixture in a solvent and recrystallization. Column chromatography may be used to resolve a phenothiazine racemate into its two enantiomers (Nilsson et al., 1994; specifically incorporated herein by reference). Racemates may also be separated using chromatographic separation, such as gas chromatography (GC) or high performance liquid chromatography (HPLC), such as used in the resolution of promethazine, ethopropazine, trimeprazine and trimpramine enantiomers (Ponder et al., 1995; specifically incorporated herein by reference). Capillary electrophoresis (CE) may also be employed (Wang et al., 2001; specifically incorporated herein by reference). Certain currently preferred methods for resolving the (+) enantiomer and (−) enantiomers of phenothiazines, including promethazine and ethopropazine, are described in the present examples.

Although the mechanism of action of the phenothiazine and promethazine enantiomers in the present invention is primarily independent of histamine inhibition, and thus different to that underlying U.S. Pat. No. 4,256,743, this patent is nonetheless instructive concerning the ability of those of ordinary skill in the art to practice the in vivo therapies of the present invention without undue experimentation, given the teachings of the present disclosure. In particular, as U.S. Pat. No. 4,256,743 concerns inhibiting bone resorption and treating osteoporosis and related bone and periodontal diseases using racemic mixtures of phenothiazines such as promethazine, and as this invention provides high efficacy enantiomers for use at lower doses, one can now inhibit bone resorption and treat bone diseases, osteoporosis and periodontal diseases using the enantiomers.

In terms of largely prophylactic uses, such as in the prevention of symptoms, or more significant symptoms, in animals and patients with indicators of disease, prophylactic or preventive doses will be employed. In terms of treatment, therapeutic doses will be used. Although achieving symptom-free states can be achieved using the invention, such end points are not a requirement of any treatment according to the present invention.

Certain of the benefits of the invention include the high efficacy, which lowers the doses required, thus reducing the cost of treatment and avoiding potential side-effects. For example, although the sedative effects of promethazine can be a drawback in certain prior art methods of use, such issues are overcome by the high efficacy provided by the invention. Moreover, the inventors further provide modified enantiomers with increased hydrophilicity, which decrease penetration across the blood-brain barrier and ameliorate negative indicators, such as sedative effects, which are mediated via the CNS.

Although the surprising effectiveness of phenothiazine enantiomers, particularly the (+) enantiomer of promethazine, in preventing bone loss could not have been predicted prior to this invention, the FDA approval for the clinical use of racemic mixtures of these drugs also provides particular advantages, shortening the path to approval for treating osteoporosis using the enantiomers, thus further lowing the cost of treatment.

Any effective means to administer or deliver the phenothiazine enantiomers, preferably the (+) enantiomer of promethazine, may be used in the methods of the present invention, i.e., in the treatment of bone loss and related diseases, such as osteoporosis, Paget's Disease and periodontitis. Preferably, it is currently believed that delivery modes to be avoided are those that favor delivery to the CNS, such as those described in U.S. Pat. No. 5,601,835, U.S. Pat. No. 5,114,719 and U.S. Pat. No. 4,883,666.

One currently preferred delivery method concerns the impregnation of the enantiomeric agents into a resorbable or non resorbable implantable matrix or transdermal delivery device that is conducive to nominal zero order release. Such matrices or delivery devices result in a substantially constant level of drug at a lower plasma concentration, thus achieving the therapeutic benefits whilst even further circumventing any possible adverse side effects. Controlled release oral formulations are also contemplated, but will typically require a higher dose at administration.

The following examples are included to demonstrate certain preferred embodiments of the invention. It will be appreciated by those of skill in the art that the compositions and techniques disclosed in the examples that follow represent compositions and techniques discovered by the inventors to function well in the practice of the invention, and thus can be considered to constitute certain preferred modes for its practice. However, those of skill in the art will, in light of the present disclosure, appreciate that many changes can be made in the specific embodiments that are disclosed and still obtain a like or similar result without departing from the spirit and scope of the invention.

EXAMPLE I

Preparation of Promethazine Enantiomers

Although various methods may be used to prepare promethazine enantiomers, the present example particularly describes methods determined to function well in the resolution and preparation of promethazine enantiomers.

In the promethazine base conversion, 100 ml ether and 25 ml 2M sodium hydroxide (0.045 mol) was added to promethazine hydrochloride (12.5 g, 0.039 mol; Sigma (lot #128H1474). The resulting suspension was shaken and the ether layer was collected. The aqueous layer was extracted twice with ether. The combined ether layers were dried over magnesium sulfate. Rotary evaporation gave 10 g (0.035 mol) promethazine. Yield 90% (step 1).

To prepare promethazine-D-tartrate, promethazine (10 g, 0.035 mol) dissolved in 80 ml acetone was heated in a 60° C. bath while dibenzoyl-D-tartaric acid (12.789 g, 0.036 mol) was added. The resulting clear yellow solution was left at ambient temperature for 3 days (step 2). A heavy precipitate formed, which was filtered off and recrystalized from ethanol four times to give 4.0 g promethazine dibenzoyl-D-tartrate white crystals (step 3).

Promethazine-D-tartrate was converted to promethazine by reaction with sodium hydroxide aqueous solution in ether. The ether layer was separated. The aqueous layer was extracted with ether and the combined ether layer was dried over magnesium sulfate. Rotary evaporation gave 1.6 g promethazine (step 4).

(−)-Promethazine hydrochloride was obtained by precipitation of promethazine with 2M HCl/ether. After vacuum drying 1.34 g off-white powder was obtained (step 5).

To prepare promethazine-L-tartrate, 11.3 g of brownish liquid was obtained from the acetone mother liquor (Step 2) after rotary evaporation. Similar to Step 4, this liquid was converted to promethazine 3.6 g (step 6). To this 3.6 g of promethazine, 36 ml acetone was added, heated in a 60° C. bath and 4.6040 g dibenzoyl-L-tartaric acid was added. The resulting clear solution was left at ambient for 3 days (step 7). A heavy precipitate formed, which was filtered off and recrystalized (three times from ethanol, once from acetone, and once more from ethanol) to give 1.2 g promethazine dibenzoyl-L-tartrate white crystals (step 7). Similar to Step 4, promethazine-L-tartrate was converted to promethazine (step 9).

(+)-Promethazine hydrochloride was obtained by precipitation of promethazine with 2M HCl/ether. After vacuum drying, 0.48 g of off-white powder was obtained (purity 99.87% by HPLC) (step 10).

Repeating Steps 1-5 with 5.7703 g promethazine gave approximately 0.95 g (−)-promethazine hydrochloride as an off-white powder (purity 99.82% by HPLC). X-ray of the promethazine racemate and enantiomers shows that the pure enantiomers are different crystal forms than the racemate. Optical rotation was measured at 27° C. in water.

EXAMPLE II

Preparation of Additional Phenothiazine Enantiomers

The present example describes methods determined to function well in the resolution and preparation of additional promethazine enantiomers.

Trimeprazine (TPZ), obtained from Sigma as the racemate, was resolved by preparative column chromatography using CHIRALCEL® OJ-H® preparative column, eluting with 99.9% methanol/0.1% diethylamine at room temperature.

Ethopropazine (EPZ), obtained from Sigma as the racemate ethopropazine hydrochloride, was resolved using the procedures in Example I.

In other studies, racemic ethopropazine hydrochloride salt was mixed with methylene chloride and 2M sodium hydroxide. The resulting suspension was agitated and the organic layer collected. After drying, the solvent was removed by rotary evaporation to give racemic ethopropazine base (4.0 g, 0.013 mol) that reacted with dibenzoyl-D-tartaric acid (4.4 g, 0.012 mol) in acetone with agitation. A white precipitate was collected after a few hours. After two recrystallization steps from absolute ethanol, a 99+% crystal was obtained, which was converted to ethopropazine hydrochloride salt. Yield: 20%. From the mother liquor, another diastereomeric salt was obtained as white precipitate, which was also recrystalized twice from absolute ethanol before converting to hydrochloride salt. Yield: 20%.

Chiral HPLC chromatograms were obtained from the recrystalized salts. One of the recrystalized salts was determined by HNMR to be the (−)-enantiomer of ethopropazine HCl. The other recrystalized salt was determined by HNMR to be the (+)-enantiomer of ethopropazine HCl.

EXAMPLE III

Inhibition of Histamine Activity by Promethazine Enantiomers

This example demonstrates that the major anti-histamine activity associated with promethazine resides in the (+) enantiomer.

$H_1$ receptor antagonist activity can be measured by a reduced production of IL-6 in controlled studies, for example, as described by Delneste et al., (1994), specifically incorporated herein by reference. In the present studies, HUVEC cells were plated and grown to confluence in 6-well plates. At confluence, the cells were treated with either histamine ($10^{-4}$M); promethazine racemate ($10^{-5}$ M) and histamine ($10^{-4}$M); promethazine (+) enantiomer ($10^{-5}$M) and histamine ($10^{-4}$M); promethazine (−) enantiomer ($10^{-5}$M) and Histamine ($10^{-4}$M) or left untreated (U/T) for 5 hours. The total RNA was isolated using Tri-reagent and subjected to reverse transcription polymerase chain reaction (RT-PCR™) analysis of IL-6 production using semi-quantitative analysis against HPRT expression (control gene).

IL-6 was produced by the HUVEC cells endogenously. Histamine alone stimulated an approximately 50% increase in IL-6 mRNA production. Promethazine racemate inhibited histamine stimulation of IL-6 production by 50% of that of cells stimulated only with histamine (i.e., approximately equal to the untreated cells). The (−) enantiomer also produced an approximate 50% reduction in IL-6 production, i.e., essentially the same as that observed for the cells treated with the promethazine racemate. The (+) enantiomer, on the other hand, reduced IL-6 production to 90% of the histamine stimulated cells. These data therefore demonstrate that the major antihistamine activity associated with the promethazine moiety resides in the (+) enantiomer.

EXAMPLE IV

Inhibition of Histamine Activity by Additional Phenothiazine Enantiomers

The present example concerns the anti-histamine activity associated with additional phenothiazine enantiomers. In particular, the example demonstrates that the major anti histamine activity associated with ethopropazine resides in the (−) enantiomer.

The IL-6 production assay using HUVEC cells was performed as described in Example III, using the ethopropazine racemate, (+) enantiomer and (−) enantiomer at $10^{-5}$M and $10^{-6}$ M. At the concentration of $10^{-5}$M, the anti-histamine activity of each of the racemate, (+) enantiomer and (−) enantiomer was so effective that resolution of the more active enantiomer could not be determined. However, conducting the assays using ethopropazine concentrations of $10^{-6}$M allowed identification of the more active enantiomer.

HUVEC cells produced IL-6 endogenously. Histamine alone stimulated an approximately 50% increase in IL-6 mRNA production. Ethopropazine racemate reduced the histamine-stimulated production of IL-6 to approximately one fifth of that observed with histamine stimulation. The (+) enantiomer was less active than the racemate, reducing the histamine-stimulated production of IL-6 to approximately two fifths of that observed with histamine stimulation (i.e., just less than that observed in the untreated cells). The (−) enantiomer, on the other hand, reduced IL-6 production to one tenth of that observed with histamine stimulation. That is, the (−) enantiomer was approximately twice as effective as the racemate and four times as effective as the (+) enantiomer. These data therefore demonstrate that the major antihistamine activity associated with ethopropazine resides in the (−) enantiomer.

The same type of IL-6 production assays were also performed using the trimeprazine racemate, (+) enantiomer and (−) enantiomer at $10^{-5}$M. At the concentration of $10^{-5}$M, the anti-histamine activity of each of the racemate, (+) enantiomer and (−) enantiomer was so effective that resolution of the more active enantiomer could not be determined. However, conducting the assays using lower ethopropazine concentrations, such as $10^{-6}$M or lower, will resolve which is the more active enantiomer, as was the case in the ethopropazine studies.

EXAMPLE V

High Efficacy Osteoclast Inhibition by the (+) Enantiomer of Promethazine

The present example describes the finding that the ability of promethazine to inhibit osteoclasts, and thus reduce bone resorption, resides in the (+) enantiomer. The example particularly describes the surprising finding that the (+) enantiomer of promethazine has a three fold higher efficacy for osteoclast inhibition than both the racemate and the (−) enantiomer.

In the osteoclast resorption assay, preosteoblasts are seeded on mammoth tusk slices and incubated in the presence of RANKL and CSF for 14 days with the addition of the respective promethazine enantiomer or racemic mixture at $10^{-5}$ M, $10^{-6}$ M or $10^{-7}$ M (FIG. 5A, FIG. 5B, FIG. 5C and FIG. 5D). During this time, osteoclasts mature and degrade bone matrix. At the end of the incubation period, cells are removed, the specimen examined by SEM and the absorption area/slice is quantitated versus control (untreated) slices.

Figure 6:
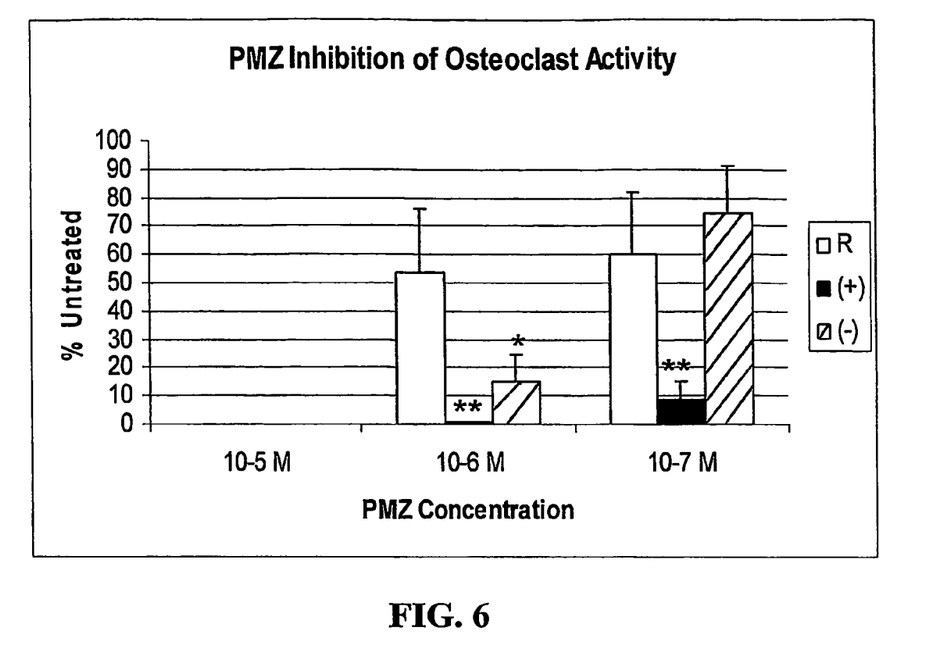
FIG. 6. Quantification of the effects of the racemic mixture (R) and the (+) and (−) enantiomers of promethazine in terms of absorption area per slice at $10^{-5}$ M, $10^{-6}$ M and $10^{-7}$ M. n=12,* $p<0.05$, ** $p<0.01$.

As can be observed visually in FIG. 5A, FIG. 5B, FIG. 5C and FIG. 5D, the (+) enantiomer of promethazine has a higher efficacy for osteoclast inhibition than the racemate and the (−) enantiomer. This data was quantified, wherein the ability of the (+) enantiomer to inhibit osteoclasts was shown to be statistically significant (FIG. 6).

For treatment of osteoporosis, a 90% inhibition of bone resorption is thus achieved with a (+) promethazine enantiomer concentration of $10^{-7}$ M. This is two orders of magnitude lower than the dosage needed for a 90% inhibition using the racemate. Significant inhibition of bone loss in postmenopausal human females was achieved using a 50 mg/day oral dose regimen (Tyan, 1993). Therefore, an exemplary daily dose of the enantiomer is nominally 0.5 mgs/day, even without compensating for the known low bioavailability of an oral route. This dose is well below the dose at which any side effects would occur and thus provides a simple remedy for reducing or eliminating bone loss.

EXAMPLE VI

Delivery Devices

This example describes certain resorbable and non resorbable implantable matrices or transdermal delivery devices that may be used to administer phenothiazine and (+) promethazine enantiomers.

Promethazine inhibits bone loss when administered as the racemate at 50 mg/day (Tyan, 1983). Ethopropazine inhibits the tremors symptomatic of Parkinson's disease at doses as high as 600 mg/day (Brocks, 1999a). At these doses, the side effects include drowsiness, dry mouth, blurred vision and constipation, all likely due to the antihistaminic and/or anticholinergic activity of these compounds. It is also recognized that the phenothiazines are highly protein bound (90-95%), rapidly metabolized to the inactive sulfoxide and other inactive metabolites, and poorly orally bioavailable (Brocks, 1999b).

The use of the more active and single enantiomer of the phenothiazine or promethazine facilitates the use of lower doses to achieve therapeutic efficacy (present Examples, particularly Example V). However, even lower doses can be used to achieve a low and constant drug titer, resulting in significant therapeutic effects with significantly less side effects.

For treatment of osteoporosis, an exemplary daily dose of a (+) promethazine enantiomer is about 0.5 mgs/day by the oral route, which is well below the dose at which any side effects would occur (present Examples, particularly Example V). Release from an implantable controlled release system, as described herein, provides phenothiazine and promethazine enantiomers active at $\frac{1}{10}$ the daily dose, based upon the current poor oral bioavailability of the compounds.

In such release systems, non-resorbable or resorbable materials are used to encapsulate the active agent for implantation or for depot use. Examples of non-resorbable materials include polyethylene copolyvinylacetate (EVA) and silicone. Resorbable materials include polylactidecoglycolydes (PGLAs), such as EcoPLA®, polycaproiactones, oxidized regenerated and others. Exemplary non-resorbable polymers are EVA fibers, as in U.S. Pat. No. 4,883,666, U.S. Pat. No. 5,801,835 and U.S. Pat. No. 5,114,719. Fiber implants such as these can be used for multi-month delivery of the optically active phenothiazines and analogues. The compounds can also be delivered in a transdermal patch format, such as the Nycoderm® or Evista® systems.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps and/or in the sequence of steps of the methods described herein, without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Barros et al., *J. Dent. Res.*, 82(10):791-795, 2003.
Brocks, *J. Pharm. Pharmaceut. Sci.*, (2):39-48, 1999a.
Brocks, *Biopharm. Drug. Dispos.*, 20:159-163, 1999b.
Delneste et al., *Clin. Exp. Immunol.*, 98:344-349, 1994.
Dobigny and Safar, *J. Cell. Physiol.*, 173:10-18, 1997.
Hall and Schaueblin, *Calcif Tissue Int.*, 55:68, 1994.

Jilka et al., *J. Clin. Invest.*, 104:439-446, 1999.
Nilsson et al., *Accta Pharm. Suec.*, 21(5), 309-16, 1984.
Ponder et al., *Journal of Chromatography A*, 692:173-182, 1995.
Rico et al., *Calcif Tissue Int.*, 65:272-275, 1999.
Schaeublin et al., *Gen. Pharmac.*, 27:845, 1996.
Tani-Ishii et al., *J. Periodontol.*, 74:603-609, 2003.
Tyan, *J. Intern. Med.*, 234:143-149, 1993.
Wang et al., *J. Sep. Sci.*, 24:658-62, 2001.
U.S. Pat. No. 4,256,743

What is claimed is:

1. A medicament comprising:
   a purified (+) enantiomer of promethazine; and
   a pharmaceutically acceptable carrier of an implantable matrix, a transdermal delivery device, or a controlled release carrier.

2. The medicament of claim 1 wherein said pharmaceutically acceptable carrier is selected from the group consisting of: an implantable matrix and a transdermal delivery device.

3. The medicament of claim 1 wherein said pharmaceutically acceptable carrier is a controlled release oral carrier.

4. The medicament of claim 1 further comprising a second anti-osteoclastic or anti-osteoporotic agent.

* * * * *